(12) United States Patent
Nieto

(10) Patent No.: US 6,595,917 B2
(45) Date of Patent: Jul. 22, 2003

(54) DISPOSABLE SPECULUM WITH INCLUDED LIGHT AND MECHANISMS FOR EXAMINATION AND GYNECOLOGICAL SURGERY

(76) Inventor: German Nieto, 1306 E. Hawthorne Cir., Hollywood, FL (US) 33021

( * ) Notice: Subject to any disclaimer, the term of this patent is extended or adjusted under 35 U.S.C. 154(b) by 152 days.

(21) Appl. No.: 09/793,269

(22) Filed: Feb. 27, 2001

(65) Prior Publication Data

US 2002/0156350 A1 Oct. 24, 2002

(51) Int. Cl.[7] .............................. A61B 1/06
(52) U.S. Cl. ........................ 600/223; 600/220
(58) Field of Search .................. 600/184, 187, 600/190, 191, 197, 199, 220, 221, 223, 225, 224, 245

(56) References Cited

U.S. PATENT DOCUMENTS

| | | | | | |
|---|---|---|---|---|---|
| 4,300,541 A | * | 11/1981 | Burgin | ................. | 600/222 |
| 4,502,468 A | * | 3/1985 | Burgin | ................. | 600/223 |
| 4,597,383 A | * | 7/1986 | VanDerBel | ............. | 600/223 |
| 4,619,248 A | * | 10/1986 | Walsh | ................. | 600/222 |
| 4,638,792 A | * | 1/1987 | Burgin | ................. | 600/223 |
| 4,884,559 A | * | 12/1989 | Collins | ................ | 600/220 |
| 5,465,709 A | * | 11/1995 | Dickie et al. | ......... | 600/223 |
| 5,499,964 A | * | 3/1996 | Beck et al. | ............ | 600/220 |
| 6,004,265 A | * | 12/1999 | Hsu et al. | ............. | 600/220 |

* cited by examiner

*Primary Examiner*—Cary E. O'Connor

(57) ABSTRACT

The disposable speculum with included light and complementary mechanisms for examination and gynecological surgery is a device used for medical and surgical procedures in the vagina, neck level and the uterus. It has two separate sheets joined in their own handles; the upper sheet has three cuts to evacuate the gases and smoke produced on the surgery area. It also has a light bulb to give clarity on the surgery area, to optimize the visibility with aluminum reflexive cover; the lower sheet has three cuts connected among themselves for an internal central channel, to evacuate the blood and fluids coming from the surgical area; the upper sheet's handle has some buttons to activate an opening and close mechanism of these sheets.

7 Claims, 15 Drawing Sheets

DISPOSABLE SPECULUM WITH INCLUDED LIGHT AND MECHANISMS FOR EXAMINATION AND GYNECOLOGICAL SURGERY

FIELD OF THE INVENTION.

The disposable speculum with included light and complementary mechanisms for gynecological examination and surgery, is a medical instrument that gives positive advantage compared with others which are used now in this health branch.

The vaginal speculum is a medical device, which is introduced through the introito to the vagina separating its walls, to be examined and making the medical or surgical proceedings easier at the vaginas neck level by sight or guided by colposcopya and of the uterus by the endoscopya.

The speculum upper sheet external face is convex, with flat surface and rounded edges to avoid pinches, that happen frequently using disposable speculas with sharp sides.

The internal face of the same sheet is concave and it has three semicircular cuts with certain distance between them, and they are connected amongst themselves for a pair of internal and lateral channels, that end in the upper right part of the proximal end which will serve to evacuate with a special vacuum (available at the market), the smoke and gases generated when any sort of gynecological surgery is practiced for vaginal tract, when cauterius are used with mono or bipolar electrodes, radio frequency or laser, this protects the medical doctor and close staff of possible contamination, making the procedure easier and shorter, because there is a better visibility.

The vertical branch or upper sheet handle has some prongs, that insert in the vertical branch or lower sheet's handle, that has some foremasts where the saw prongs will rest when the speculum is open to make the visual and the examination area bigger. In order to make the speculum opening smaller, it is necessary to press on a button that makes the prongs come out and move away from the foremast, sliding the upper sheet's vertical branch on the lower sheet's vertical branch, and to close the specula and remove it without pain, pressure has to be made on the other button to unblock the upper sheet.

The lower sheet's external face is convex with flat surface and rounded edges, too. The internal face of the same sheet is concave, and it has three semi-circulars cuts with certain distance between them, connected amongst themselves for an internal oval flat channel, which ends in the lower extreme of the sheet's descendant branch, where it turns into a round channel where the blood, that is originated from the surgical area through a vacuum designed for this proceedings, is evacuated, making them more comfortable easier and faster, avoiding the dryness and the clearing of thief sloped place where the blood is accumulated. If this end is not connected to a vacuum, it can also be connected to make the blood flow through gravity. Joined to the previously described, and to optimize the visibility of surgical and examination area, in the upper sheet's internal face, in the center, and on the space between the two first cuts, there is a light bulb, which given its nearness to the surgical area, will offer clarity and because of its localization will not interfere with the surgical proceedings. The light bulb is protected to avoid damage by the instrumental, and it has a thermal isolation to avoid heat up of the speculum upper sheet, which would cause injuries on the vaginal mucous. The internal face of the anterior portion close to the light bulb has an aluminum reflexive cover (a metal covering vacuum technique with aluminum) which will offer an excellent lighting. The speculum has to be made of dark non-reflective material when used in laser proceedings.

INVENTION BACKGROUND

Convinced by my personal experience as a gynecologist, that many patients don't attend appointments of this specialty and don't take a cytology, because they are afraid to be hurt when the speculum is used; in some cases problems are created due to the designs of some disposable speculum and reusable metal specula that make their use difficult, not practical for the medical doctor and uncomfortable for the patient, in many cases producing small injuries that cause discomfort for the patients which give a bad reputation to these devices.

The vaginal speculum is a device which is introduced through the introito to the vagina separating its walls to be examined and making the medical or surgical proceedings easier at the vaginas' neck level by sight or guided by colposcopya and of the uterus by the endoscopy.

Some speculums have ungentle edges and their surface is rough causing sometimes pinches of the vaginal mucous and on the smaller and bigger lips. Others have their sheets separated which makes them unstable when they are introduced in the vagina, causing discomfort to the patients and not allowing the specula to open on their distal end if it is required, to expand the surgery field and examination area. Some of them have the handle's lower end of the lower sheet with a forward curvature, being this the support point to handle and open the speculum, which allows the contamination of the gloves due to their closeness to the anal and perianal area, besides to cause discomfort to the patients. The same happens with the other ones that have a mechanism to open the sheet's that consist in a curve piece with prongs on the upper sheet's handle, which introduces itself in a cut of the lower sheet handle, producing similar effect as the previous one. In both previous cases if the medical doctor doesn't take precautions to change his gloves and proceed to practice a vaginal tact like a complement of the examination, he would be contaminating the patient with possible anal pathology to the vaginal area, and with possibilities of propagation to the pelvic area, with their consequences sometimes irreversible from the medical point of view, like for example, pelvic inflammatory chronic illness, infertility caused by tubary obstruction among others and they seem expensive from the economic point of view.

The speculum proposed by me, has rounded edges and fat surface and has an opening mechanism comfortable and fast for the upper sheet, the same works to enlarge the distance, between the both sheets, giving wideness to the surgery or examination area. The lower sheet's handle has in its distal end an elbow shaped handle to avoid discomfort to the patients in the anal and perianal area, and therefore with out contamination.

In regards to the portable lighting which come from the light bulbs, which are located on the speculum upper sheet and which after each examination are removed and used again with other patients, open the possibility for contamination even with precautions. The same would happen in other prototypes of reusable lighting, where the light is attached to the upper sheet's internal face with adhesives used for these cases.

The lighting proposed by me, would be included in the disposable speculum upper sheet internal face through a small light bulb localized between the two first cuts, and it will be feed through a plug located on the back end and upper right of the speculum upper sheet. The light bulb has a thermal isolation to avoid injuries of the vaginal mucous membrane, and also because of its proximity to the surgical area, it will give an excellent lighting that will help to make the procedures easier. The internal face in the front part at the light bulb has an aluminum reflexive cover (aluminum metal vacuum technique) which will have effect on an very good lighting. When the speculum is used in proceedings with laser, it has to be made with a dark and no reflexive material.

There is a pipe system for the smoke and gases suction which are generated in specific gynecological methods through vaginal via, but its surface is not too big.

Thinking about the high incidence of bacterial, micotical and viral illness in the gynecological area, and that some of these are involved in the feminine cancer etiology, and that in many cases the practice of methods using cauterius, radio frequency or laser, is necessary, generating smoke and gases that can be sources of contamination, the speculum described has in the upper sheet's internal face three cuts (to a certain distance each one) separated one of another by a certain distance and internally connected by a pair of channels designed to evacuate them through a special vacuum, also improving the visibility, having as a result a less time investment.

The cut's surface of the speculum proposed by me, is big because of it semicircular form, and because they are distributed along of the upper sheet and bilaterally and internally connected will have a bigger absorption surface, a bigger utility and effectiveness.

It also has three cuts on the lower sheet's internal face that will drain the blood and liquids originated from the surgery area, whether vaginal, cervical, or when they practice uterine endoscopes, making faster proceedings, avoiding the drying and cleaning at intervals of the surgical area, specially in these last ones, where large amounts of liquids are used. To make the speculum use faster and comfortable, some bottoms have been designed, which by pressing make the opening and closing of it easier.

The ideal would be a prototype of speculum, which would have included all the necessary mechanisms for examination and gynecological surgery through the vaginal tract, and easily disposable later, because this area sometimes is highly contaminated by sexual transmission illnesses, bacteria, fungus, and virus, some of these involved in the feminine genital cancer etiology.

The prototype of the disposable speculum created by me, offer and join these advantages.

BRIEF SUMMARY OF THE INVENTION

It is about a disposable speculum with included light and complementary mechanisms for examination and gynecological surgery; which offers positive advantages compared with the ones which are actually used in this health branch.

As a gynecological medical doctor, I am concerned for practicing an excellent exam, looking for the patient's and our comfort, which will have optimum results that will change the preconceived negative mentality of our dear patients for this type of exams and procedures, making them more agile and that using the specula is not traumatic, I decided to propose a prototype of a plastic transparent disposable speculum, which includes several requirements for such purposes.

The speculum upper sheet external face is convex, of flat surface and having rounded edges to avoid pinches, which are so common with the disposable speculum that does not have delicate edges. The internal face of the same sheet is concave and has three semi-circulars cuts at a certain distance between them, and connected through a pair of lateral internal channels which end in upper right area of the proximal, which will serve to evacuate with a special vacuum (available in the market) the smoke and gases produced when any kind of gynecological surgery through the vaginal tact is practiced, where cauterys are used, monopolar or bipolar electrodes, radio frequency or laser, protecting de medical doctor and near staff of possible contamination, making the procedure easier and shorter and offering a better visibility.

The external face of the lower sheet is convex with a flat surface and has it also has its rounded edges. The internal face of the same sheet is concave and has three semicircular cuts at a certain distance amongst themselves, connected between them by an internal oval, flat channel which ends in the lower end of the descendent branch of the sheet where it becomes in to a round channel through which the blood produced on the surgical area is evacuated through a vacuum used for this procedures, making them easier and faster and avoiding the drying and the cleaning of the places where the blood is accumulated. If this end is not connected to a vacuum, it can be connected to a container through a hose and the blood will flow by gravity. The vertical branch or upper sheet's handle has some prongs in it and they fit in the vertical branch or lower sheet's handle which has some foremasts where the saw prongs are inserted when the specula is opened to expand the visual and examination field. In order to reduce the specula's opening, pressure is made on a button that forces the prongs to go out and separate from the foremasts sliding the vertical branch of the upper branch into the lower sheet's vertical branch; to close the speculum and remove it without discomfort pressure has to be made over another button that unlocks the upper sheet.

Joined with the previous, and in order to optimize the examination area or surgery area visibility, on upper sheet's internal face, centrally and in the space between the two first cuts, there is a small light bulb which, given it nearness to the surgical area, will give clarity and because of its localization, will not interfere on the surgical procedure. The light bulb is protected to avoid damages with the instruments and has a thermal isolation to prevent the specula's upper sheet to be heated because it would create injuries on the vaginal mucous.

DETAILED DESCRIPTION IN THE INVENTION

Figure 1:
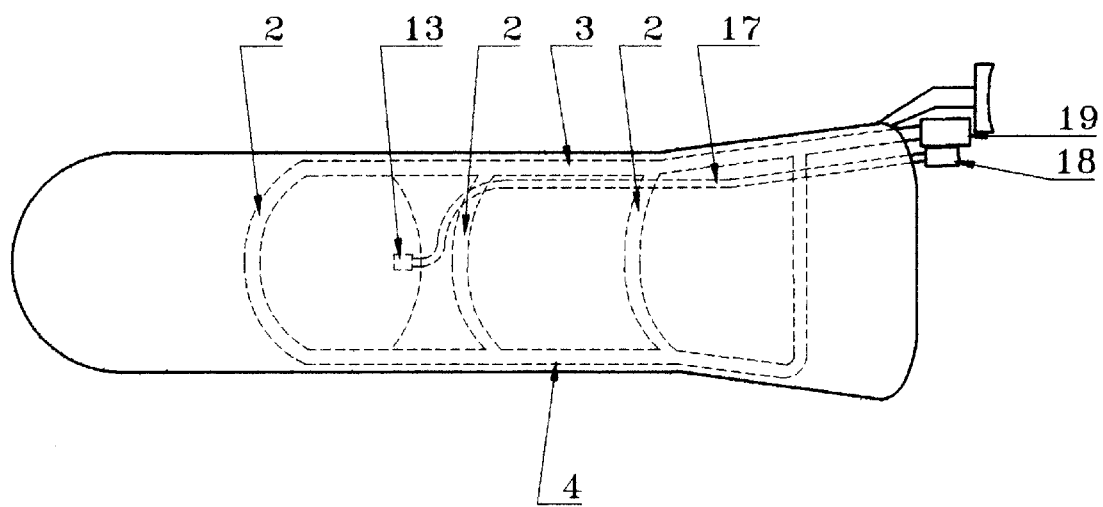
FIG. 1 corresponds to an upper view of the speculum upper sheet.
Figure 2:
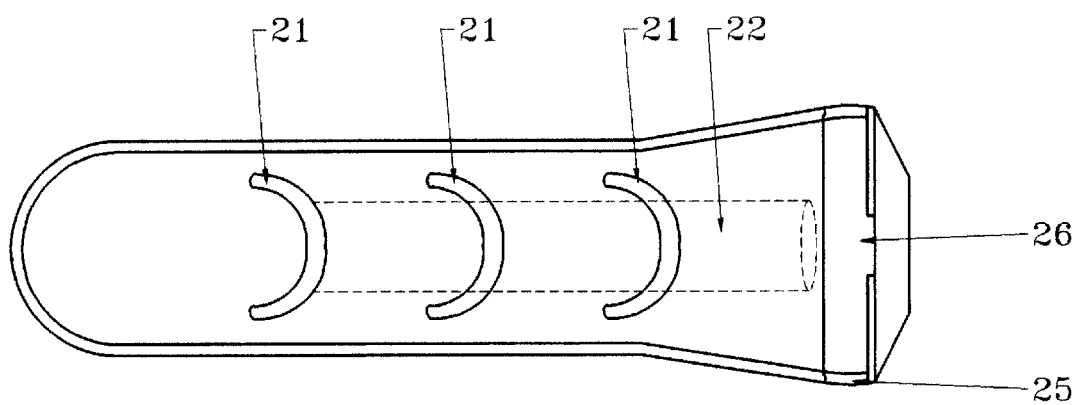
FIG. 2 corresponds to an upper view of the speculum lower sheet.
Figure 3:
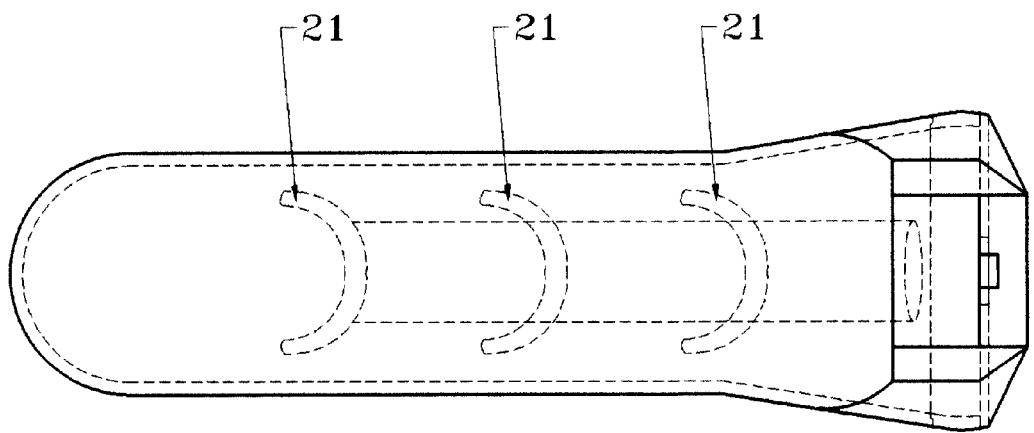
FIG. 3 corresponds to a lower view of the speculum.
Figure 4:
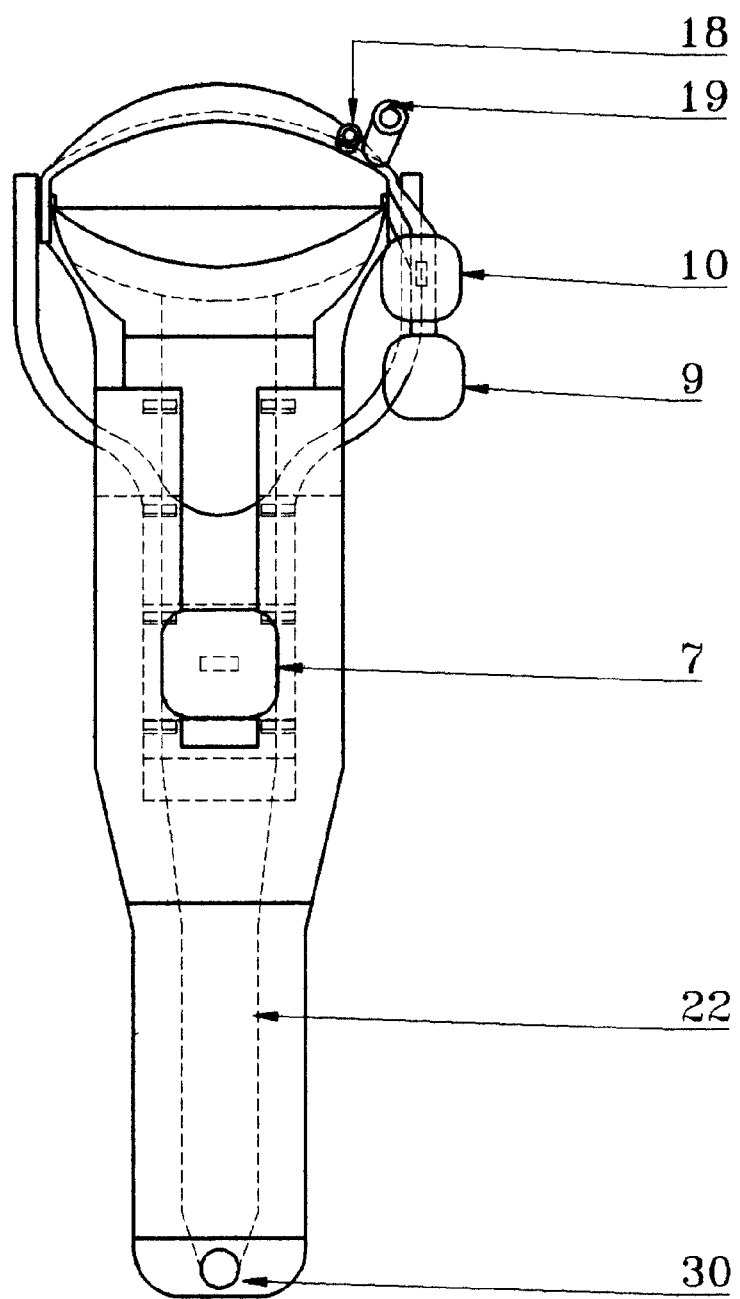
FIG. 4 corresponds to a back view of the speculum.
Figure 5:
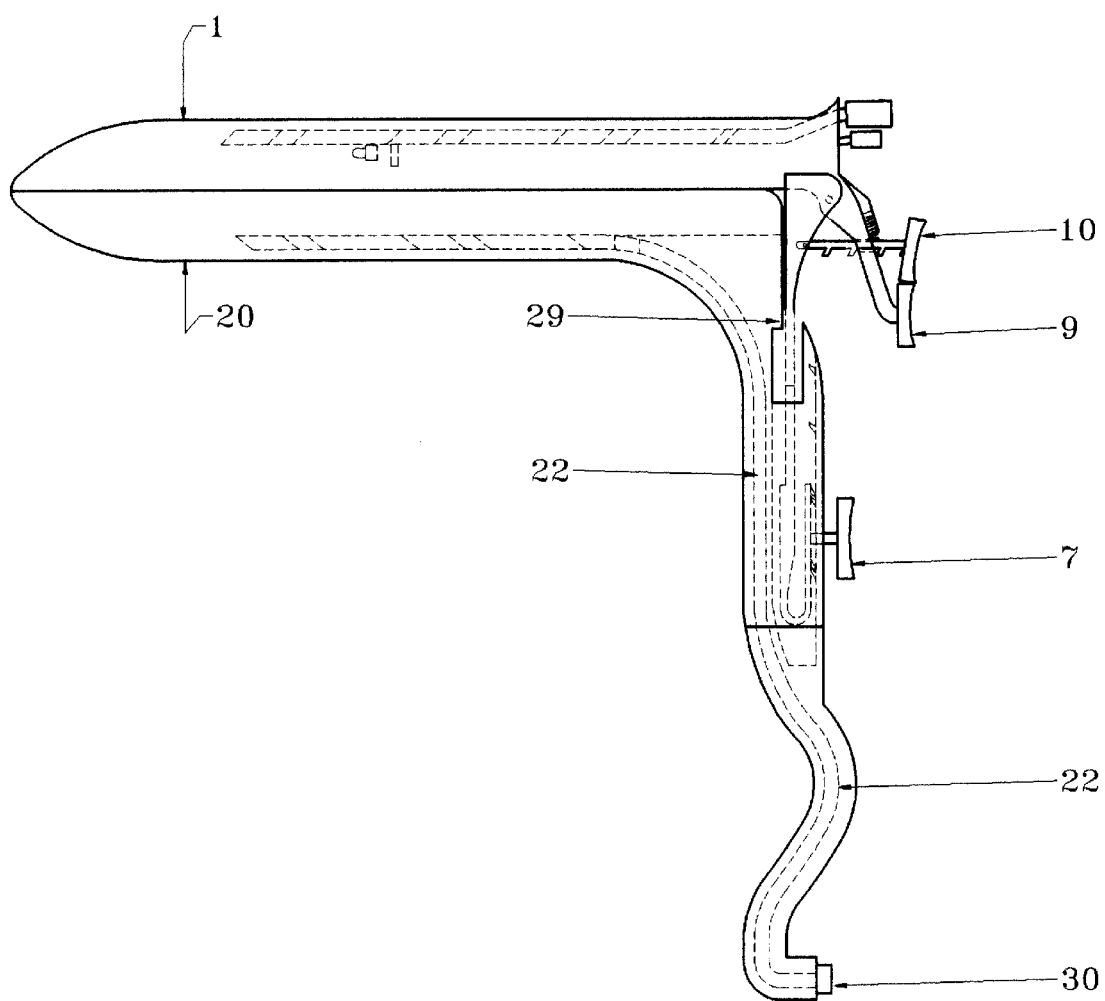
FIG. 5 corresponds to lateral left view with the speculum.
Figure 6:
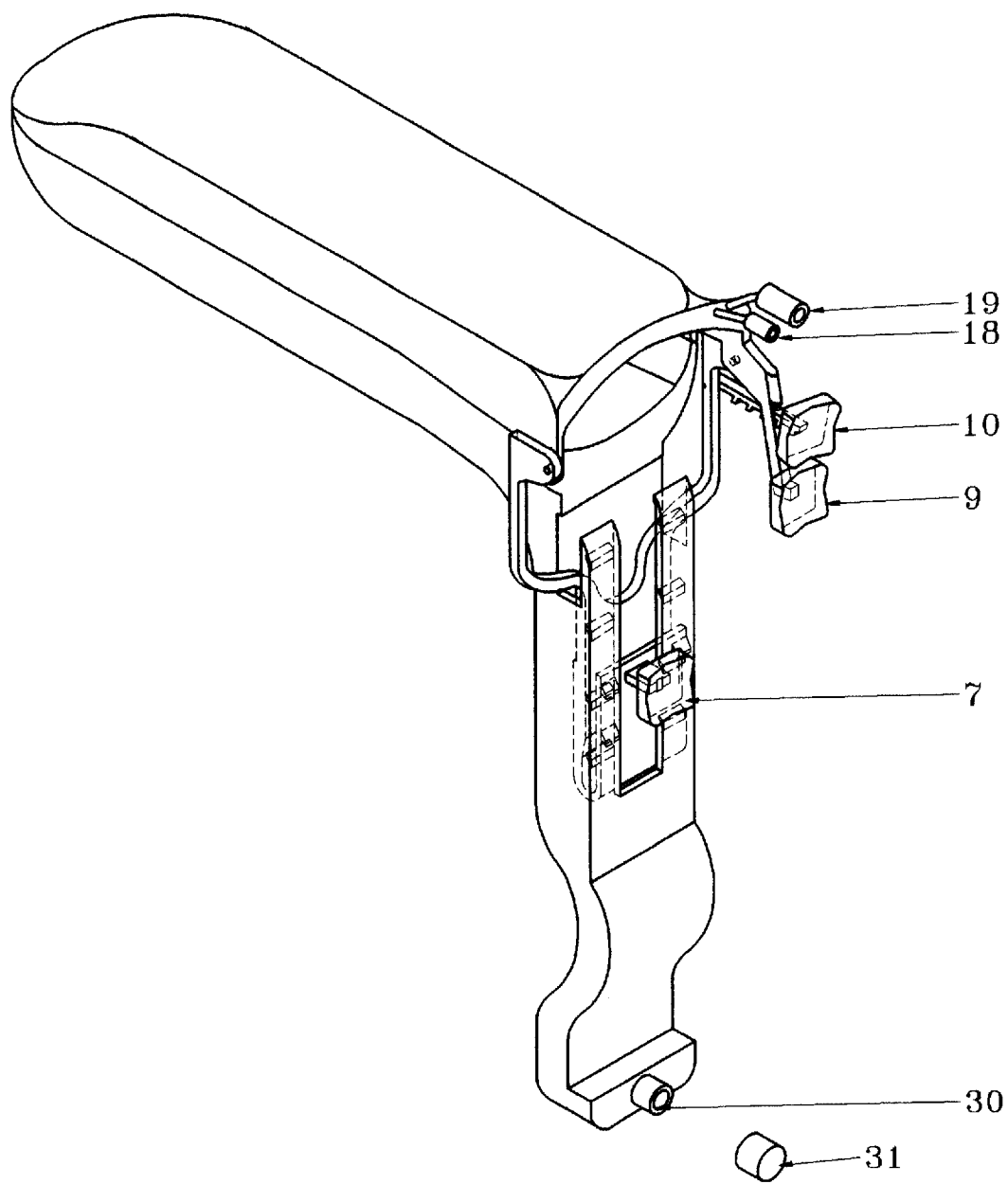
FIG. 6 corresponds to an isometric perspective of the speculum.
Figure 7:
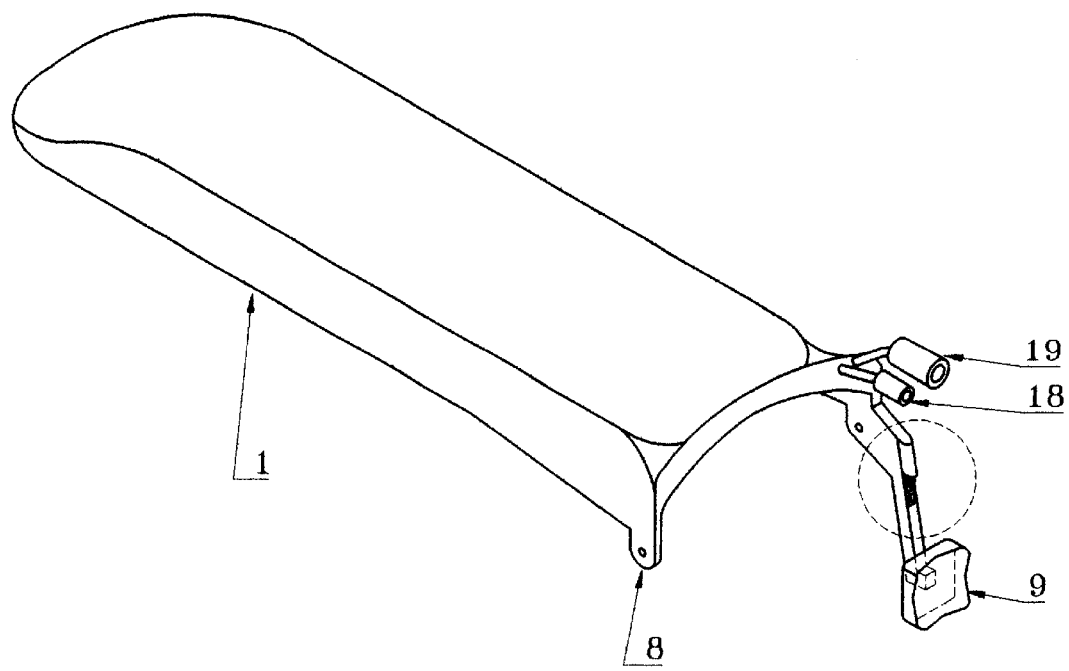
FIG. 7 corresponds to a perspective view of the upper sheet of the speculum.
Figure 7A:
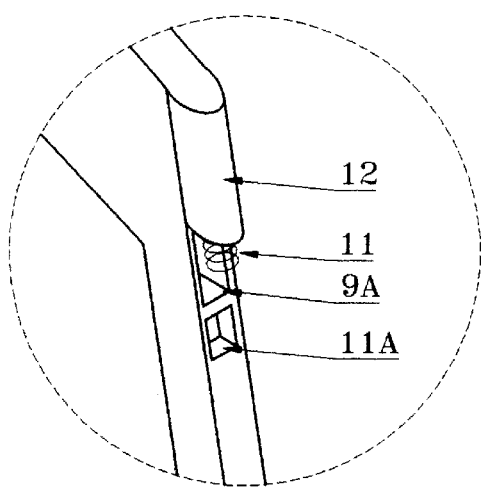
FIG. 7A corresponds to a detailed view of a part of the right lateral extension.
Figure 8:
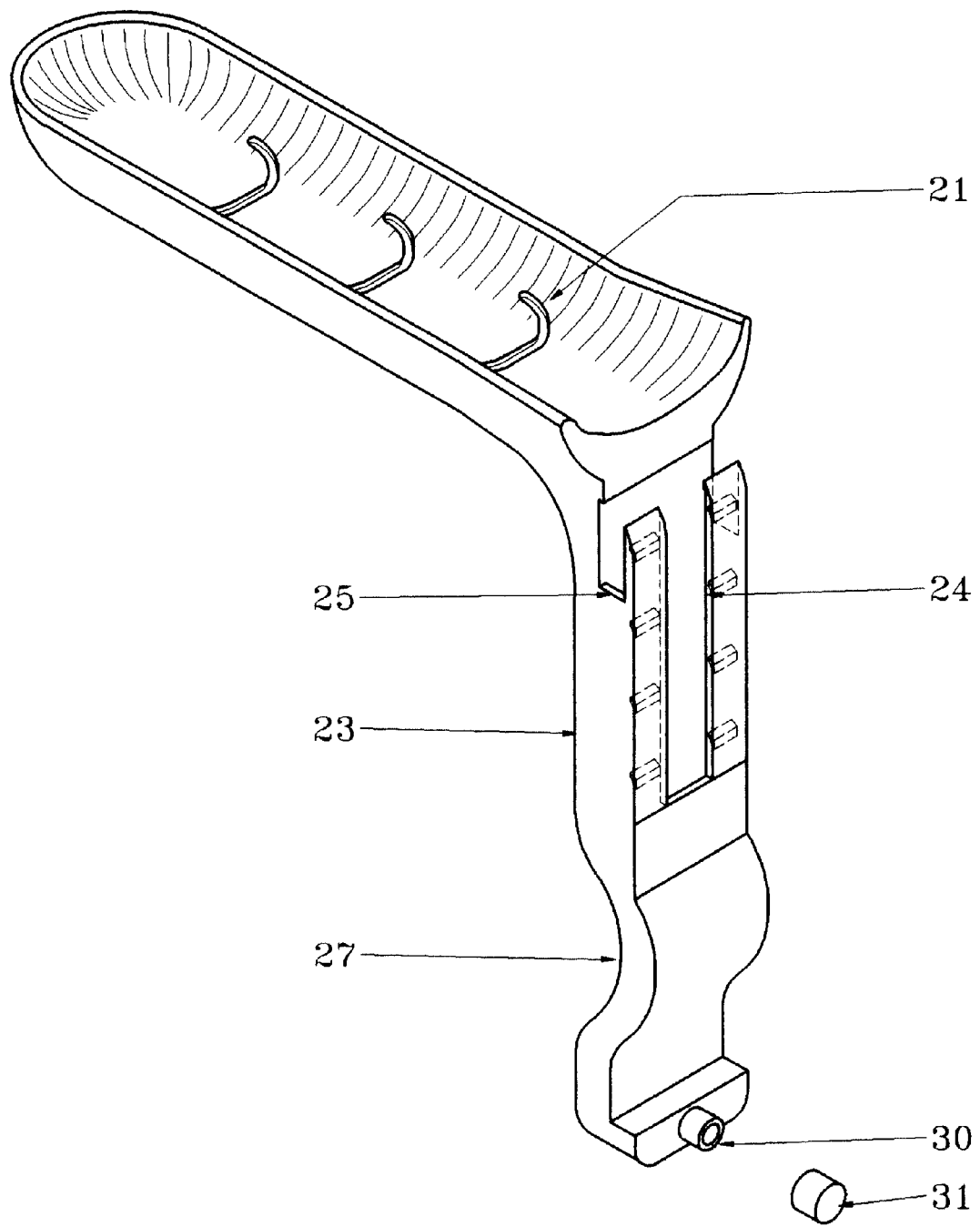
FIG. 8 corresponds to an isometric perspective of the lower sheet.
Figure 9:
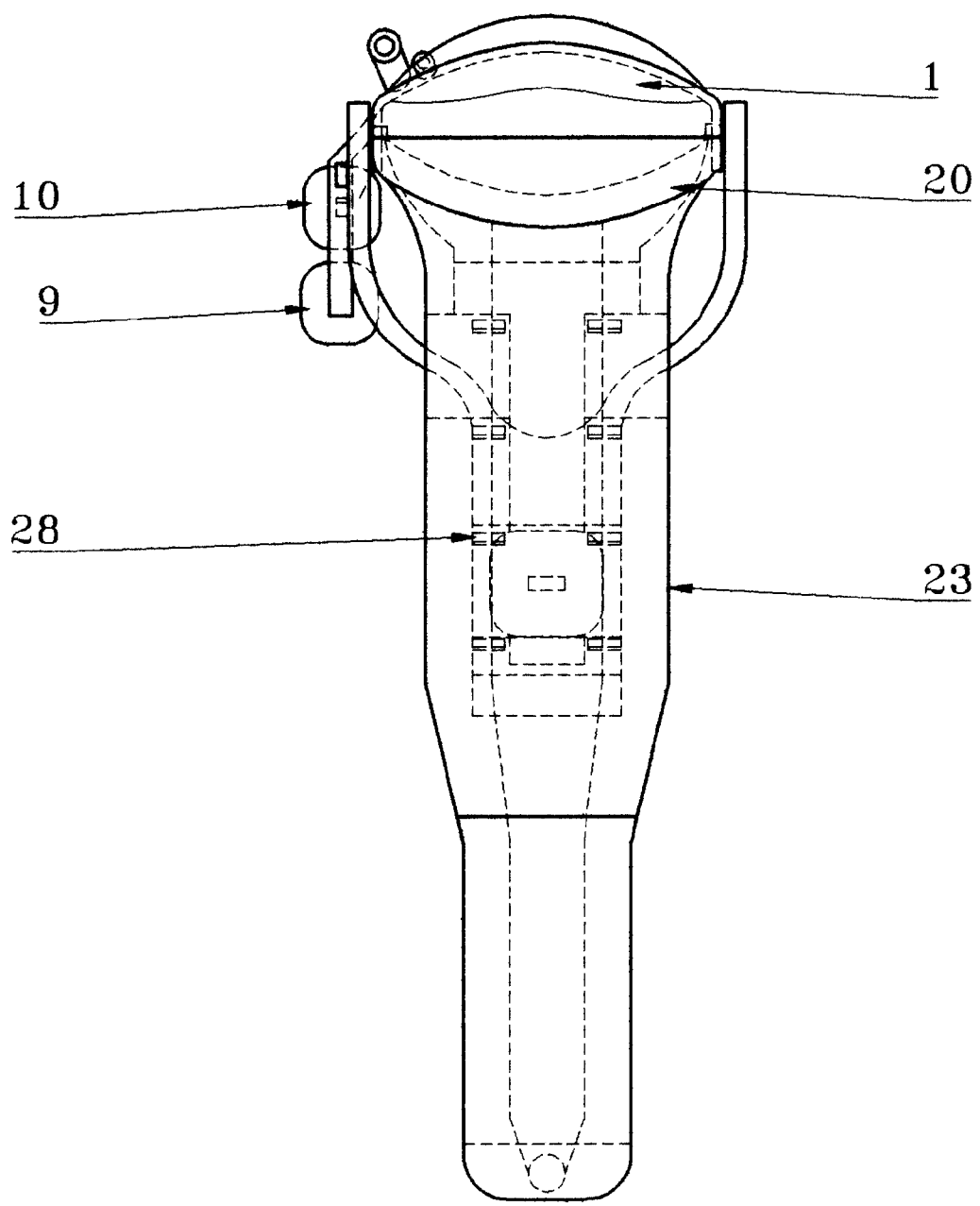
FIG. 9 corresponds to a frontal view of the speculum.
Figure 10:
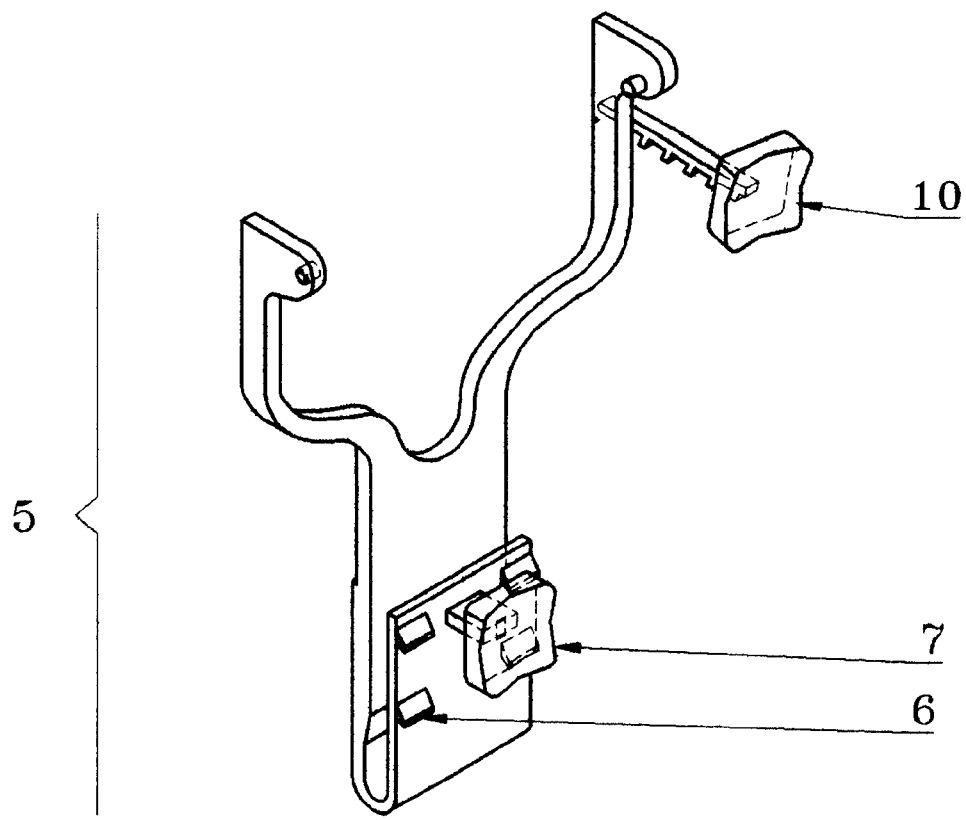
FIG. 10 corresponds to isometric perspective of the back handle.
Figure 11:
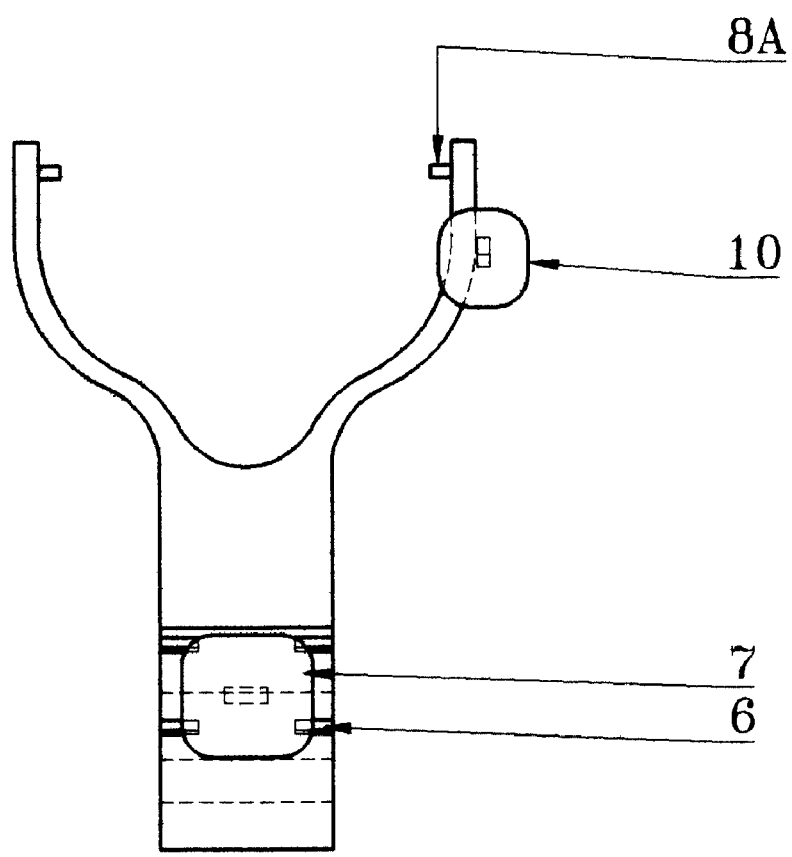
FIG. 11 corresponds to a back view of the back handle.
Figure 12:
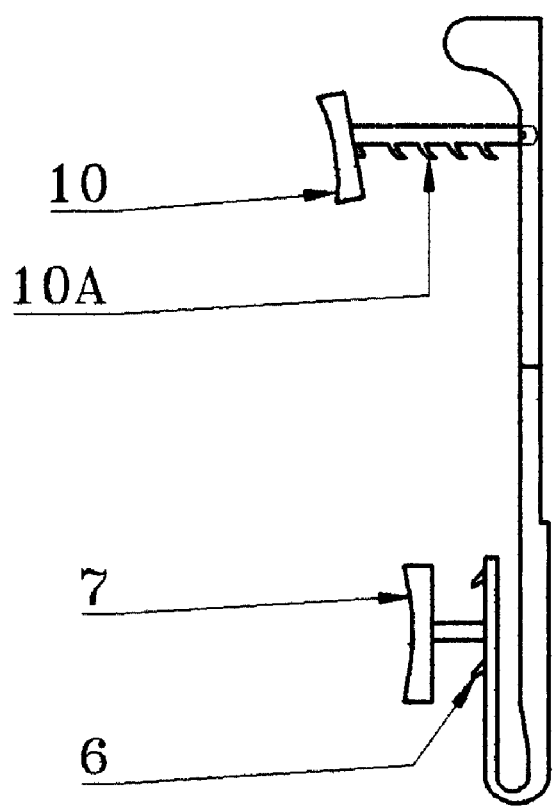
FIG. 12 corresponds to a lateral right view of the back.
Figure 13:
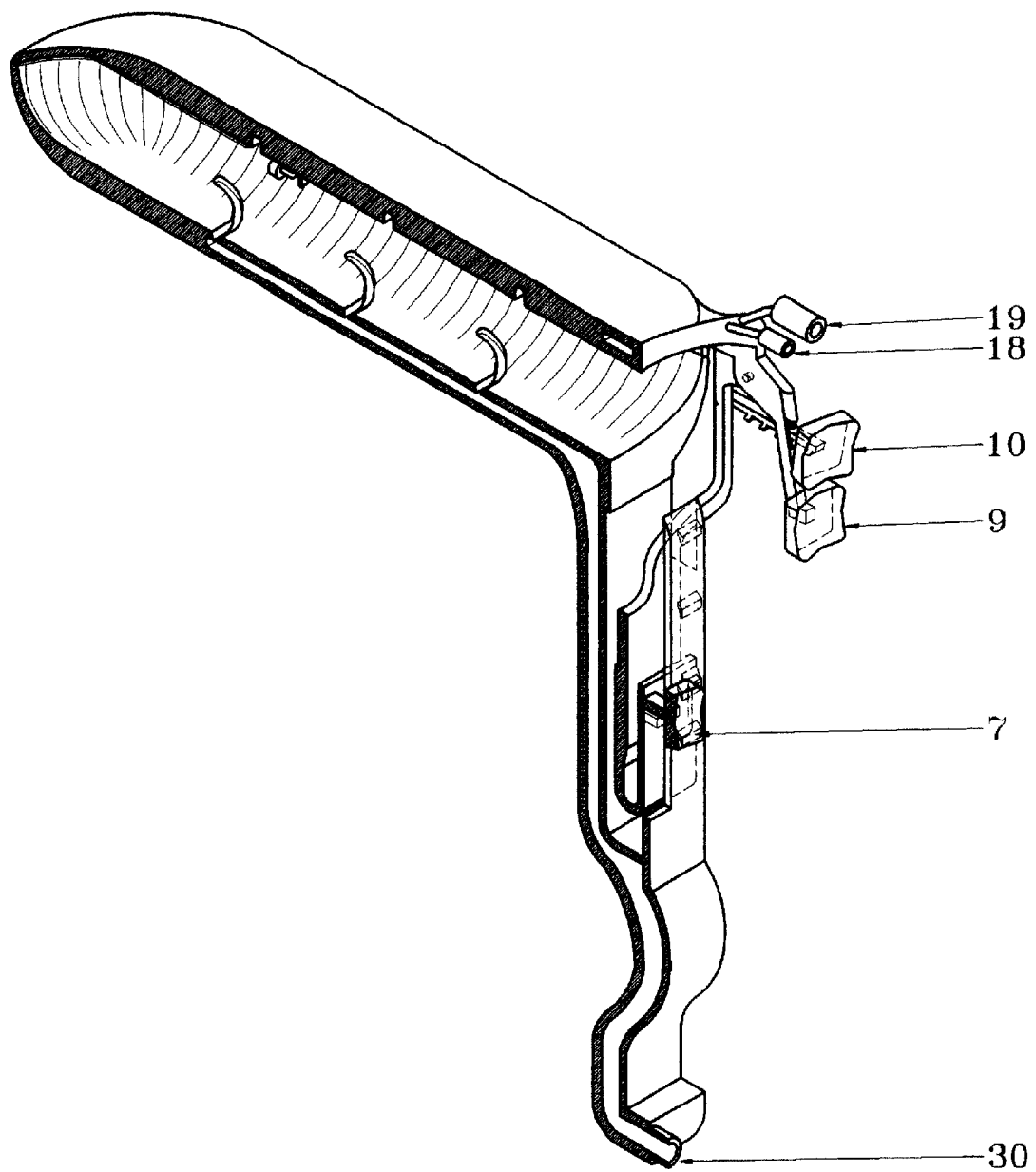
FIG. 13 corresponds to an isometric cut of the speculum.
Figure 14:
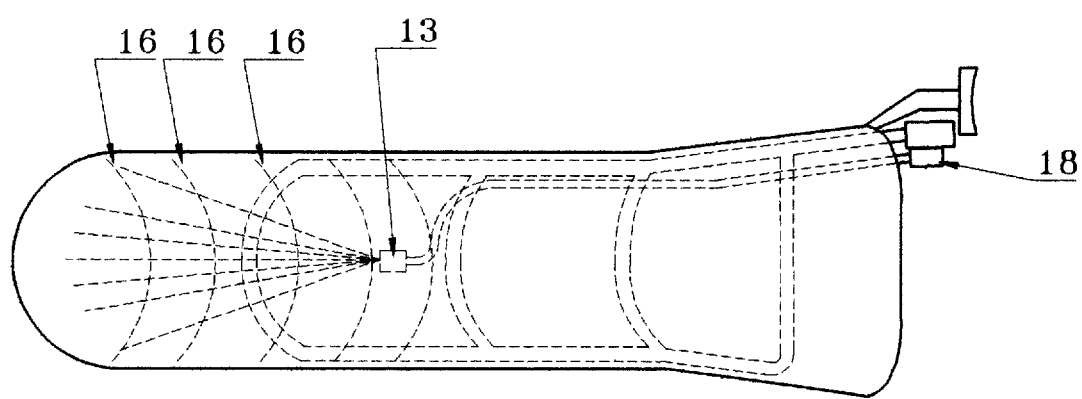
FIG. 14 corresponds to an upper view of the specula's upper sheet.
Figure 15:
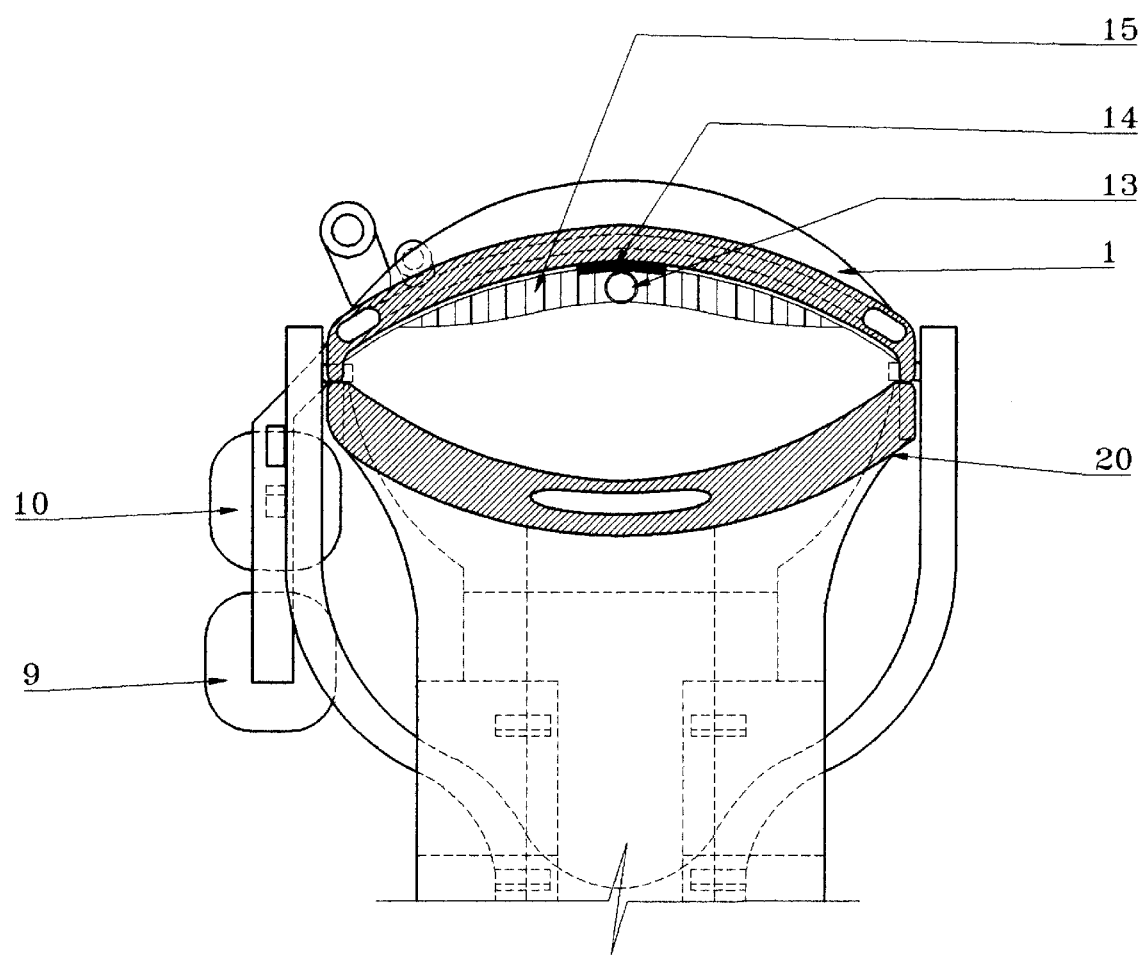
FIG. 15 corresponds to a cut of the specula at its lighting system level.

It is very important to know the different parts that make up the disposable speculum therefore they will be listed:

1. Upper sheet (mobile).
2. Cuts in the internal face (front, middle and back) of the upper sheet, to suck the smoke and gases coming from the surgery area.
3. Right internal lateral channel, which joins the three cuts of the upper sheet.
4. Left internal lateral channel, which joins the three cuts of the upper sheet.
5. Vertical branch or back handle of the upper sheet.
6. Saw prongs of the handle of the upper sheet.
7. Button shaped end to open and close the upper sheet.
8. A whole where the upper sheet's back handle is articulated.
8A. Axis to articulate both sheets.
9. Lateral right extension of the upper sheet with its button shaped end to move away the same.
9A. Hole space or opening where the automatic safety device goes through.
10. Upper sheet's automatic device with its shaped end button to unlock it.
10A. Automatic safety's prongs.
11. Plastic spring of the automatic safety.
11A. Space where the automatic safety's prongs insert.
12. Cylinder or space where the spring goes.
13. Upper sheet's light bulb.
14. Light bulb thermal isolation.
15. Light bulb's protection.
16. Reflexive covering with aluminum in some part of the upper sheet's internal face.
17. Channel where the cable which joins the light bulb with the plug is introduced.
18. Plug for the pin of the light source.
19. Plug to drainage the smoke and gases.
20. Lower sheet.
21. Cuts on the internal face (front, middle, and back of the lower sheet to suck the blood originated from the surgical action.)
22. Internal central oval flat channel that joins the three cuts of the lower sheet.
23. Fixed vertical branch or front handle of the lower sheet.
24. Back cut of the Handle of the back sheet.
25. Bi-lateral cuts on the handle of the lower sheet.
26. Upper half of the handles of the lower sheet which has a space where the upper sheet's handle goes.
27. Elbow shaped of the front handle.
28. Foremasts of the lower sheet's handle.
29. Internal front flange on the vertical branch or front handle of the lower sheet which avoids the vertical branch or back handle going out of its place.
30. Plug for the blood drainage.
31. The drainage plug's cap.

In many cases the gynecological examination turns difficult because a part of the consulting and gynecological pathology and the majority of the gynecological surgery through the vaginal tract, entails genital bleeding which will interfere in the suitable observation, making necessary cleaning and drying the surgical or examination area with certain frequency and depending of the intensity of the bleeding, many times it flows through the speculum lower sheet towards the outside, contaminating the table and everything else and making the process difficult and delayed. The same happens when diagnosis procedures are practiced endoscopies or surgical endoscopics of the uterus, in which liquids have to be used to expand the cavity and to be improve the visibility. This also happens in procedures where the cauterys, the electrodes monopolares, the radio frequency or the laser is used; in the surgery area smoke and gases are generated that difficult the visibility and, which is worst, when there are virus involved in the pathology to be treated, some of them related with feminine genital cancer, creating microparticle for them, that can to contaminate to the medical doctor and the staff around.

Thinking about the previous matters, I have created a prototype of disposable speculum which not only will facilitate the examinations and medical procedure and/or surgical gynecological, but it also avoid contamination and it will make the process less length, which in a given moment are traumatic for the patients.

The disposable speculum mentioned, is of transparent plastic material and consist of upper sheet (1), mobile, with the external face of convex shape, of flat surface and round edges; its internal face is concave and has three cuts (2): front, middle and back, semicircular, joined between them by a pair of laterals internal channels: right (3) and left (4) which end in a plug (19) which goes to a special vacuum, which will drain the smoke and gases produced in the surgery area. The upper sheet also has a right lateral extension (9) obliquely oriented and downwards in an angle of 30 grades approximately, that is used to open the speculum and to move separate the vagina's walls in order to practice a complete examination of them, of the cervix and the fornix. The lateral extension has a space or opening (9*a*) where a mobile safety bar shaped goes through (10), which comes from the lateral middle part of the vertical branch of the upper sheet. That bar has in its lower flat face semi-curved prongs (10A) with their tips forward, which are inserted in a space (11A) of the lateral extension located in the back part and lower to the opening pushed by a plastic spring (11) which is in of the cylinder (12) located in the upper back part at the opening of the same extension.

The vertical branch or back handle (5) of the upper sheet has a fork shape. Its upper end (8A) articulate for both sides to the proximal end (8) of the upper sheet to give it mobility when opening and closing the speculum. The lower part of that handle has handleshape, being its back branch shorter and which has saw prongs (6) at both sides with their tips downwards, which insert in a foremasts (28) when a button, for this purpose, is pushed forward, upward and downward.

The upper middle of the fixed vertical branch or front handle (23) of the lower sheet has semicircular shape and is hollow to hold the back handle. (5) It has a back cut (24) where it is pulled in and slides the back handle's button (7). Internally at both sides of the cut has some foremasts (28) where the saw prongs (6) of the back handle go. Bilaterally there is a cut (25) where partially the fork of the back handle is inserted (5). The lower part of the front handle has an elbow shape (27) where the ring finger is placed facilitating its handling and avoiding contamination. In the anterior wall of this handle and internally the channel goes down (22) to evacuate the blood and liquids which come from surgery area or from the examination.

To close the upper sheet pressure needs to be made upwards on the button shaped end of the safety devices (10) and it will close by the action of the muscles of the vagina, the anal and perineal elevators, controlling with the thumb finger the gentle closing, because both buttons, that is, the one for opening the speculum (9) and the and the one of the safety device (10) are close one of another. All the buttons have concave shape, and they adjust itself better to the thumb finger to-press to open or to close the speculum.

The low sheet (20) is convex externally, with flat surface and rounded edges. Its internal face is concave and has three cuts (21): frontal, media and back, semicircular, joined between them by a central internal oval flat channel (22) which goes down by the frontal side of the vertical branch or handle (23) of the lower sheet; and by its lower rounded end (30) the blood on liquids will be evacuated from the surgical area or from the examination, when this channel is connected to a vacuum or by gravity to a small bottle. This end has a cap (31) for when it is not used to drain.

Looking for a optimum lighting, the internal face of the upper sheet has a small light bulb (13) centrally located between the two firsts cuts, with a thermal isolation (14) to avoid injuries on the vaginal mucous when the sheet becomes warm and to keep the light bulb protected (15) of damages that could happen to it with the instruments. The internal face in the place in front of the light bulb has a reflected cover (16) with aluminum (a metal covering vacuum technique with aluminum), what has effect on a very good lighting. The light bulb receives through a plug (19) the electric current feed by a source of conventional light.

FIGURES DESCRIPTION

The figure N° 1: shows a upper view of the speculum upper sheet where the N° s 2 belongs to the anterior and back cuts, the N° s 13 belongs to the light bulb located between the two first cuts; the N° s 3 and 4 belongs to the lateral channels right and left respectively, with the N° 17 the channel with the cable which joins the light bulb with the plug N° 18 and with N° 19 the plug through where the smoke and gases and generated in the surgical area are sectioned FIG. N° 2 shows us a upper view of the speculum lower sheet where the N° s 21 belong to the font, medium and back cuts, the N° 22 (dotted lines) the flat oval channel which joins the cuts, and where the blood which comes from the surgical area is drained, the N° 26 shows the space where the back handle goes, and the N° 25 the bilateral left cut on the lowers sheet's handle.

We can see in the figure N° 3 a lower view of the speculum where the N° s 21 show us in dotted lines, the medium, and back cuts.

FIG. N° 4 belongs to a back view of the speculum where N° 18 shows us the plug for the light source's pin, N° 19 belongs to the plug to drain the smoke and gases; N° 10 belongs to the automatic safety of the upper sheet, N° 9, the lateral right extension of the upper sheet, N° 7, the button end to open and close upper sheet, N° 22 to the central internal oval flatted channel, that joins the three cuts of the lower sheet and N° 30 belongs to the plug to drain the blood.

FIG. N° 5 shows us a lateral left view where N° 1 belongs to the upper sheet, N° 20 belongs to the lower sheet of the speculum, N° 29 belongs to the internal edge of the front handle, which holds the back handle, N° s 9 and 10 belong to the open and safety buttons respectively, with N° 7 the back handle's button and with N° s 22 and 30 the oval channel which joins the three cuts and the drainage plug, respectively.

In FIG. N° 6 we see in a isometric perspective of the speculum where N° 19 belongs to the drainage's plug of smoke and gases, N° 18 belongs to the plug for the pin of the light source. N° s 9 and 10 to the opening and upper sheet safety buttons, with N° 7 the back handle's button and with N° s 30 and 31 the drainage round plug and the its cap.

In FIG. N° 7, we have a perspective view of the upper sheet marked with N° 1, with N° s 18 and 19 the plug for the light sources pin and the plug for the smoke and gases drainage, respectively and N° 9 open button to the upper sheet and N° 8 the hole where the back handle axle of the upper sheet goes, making a joint.

In FIG. N° 7A we can see in detail a part of the lateral right extension where N° 12 belongs to the cylinder where the spring fits, N° 11 the spring, N° 9A the opening or space where the automatic safety goes through and N° 11A the space where the safety prongs fit.

In FIG. N° 8, we observe an isometric perspective of the lower sheet with its anterior handle pointed out with the N° 23, with N° 21 the posterior cut, N° 24 the place where the back handle goes in to the upper sheet, N° 27 belongs to the elbow shaped of the frontal (anterior) handle, N° 30 the place of the blood and fluids drainage and N° 31 its caps.

FIG. N° 9, shows an anterior view where N° 1 belongs to the superior sheet, N° 20 to the inferior sheet N° s 9 and 10 to the open and the safety buttons of the superior sheet N° 28 to the handle's foremasts of the inferior sheet and the N° 23 to the anterior handle.

In FIG. N° 10 we can see an isometric perspective of the posterior handle and its different parts, marked with N° 5. N° 10 points out the automatic safety device of the superior sheet with its button end to unblock, with N° 6 the saw like prongs which introduce them selves in the anterior handles' foremasts when the marked button is activated, with the N° 7 to open or close the speculum.

In FIG. N° 11 we observe a posterior view of the posterior handle where N° 8A belongs to the axle which articulates with the posterior end of the superior sheet, N° 10 out the automatic safety device of the superior sheet, N° 10 the button to open or to close and the N° 6 to the saw prongs of the superior sheet handle.

In FIG. N° 12 we have a lateral right view of the posterior handle where we observe with the N° 10 the automatic safety device, with the N° 10A the prongs of the posterior handle, with the N° 7 button to open or close the superior sheet and the N° 6 the saw prongs of the same handle.

In FIG. N° 13 we observe an isometric section which points out with the N° 19 the drainage's plug for smokes and gases, with N° 18 the plug for the light source, with N° s 10 and 9 the buttons to open and to close the speculum superior sheet, with the N° 7 the button to lift up or bring down the superior sheet which gives more space and visibility, and with the N° 30 the plug of the blood and fluids drainage.

In FIG. N° 14 we have a superior view of the superior sheet, with N° 16 the aluminum reflexive cover in part of the internal face of the superior sheet, with the N° 13 the light bulb and with the N° 18 the plug for the light source.

In FIG. N° 15 we observe a speculum section at the lighting system level, where N° 15 belongs to the light bulb protection, N° 14 the thermal isolation's light bulb, N° 13 the light bulb, N° 1 to the superior sheet, N° 20 to the inferior sheet, N° s 10 and 9 to the buttons to open and close the superior sheet.

References Cited

U.S. PATENT DOCUMENTS

| | | | |
|---|---|---|---|
| 4,807,600 | February, 1989 | Hayes | 128/17 |
| 5,179,937 | January, 1993 | Lee | 128/17 |
| 4,067,323 | January, 1978 | Troutner, et al. | 128/18; 128/23; |
| 5,509,893 | April, 1996 | Pracas | 600/224; 600/184; |
| 5,329,937 | July, 1994 | Krstevich, et al. | 128/17; 128/3; |
| 5,743,852 | April, 1998 | Johnson | 600/207; 600/184; |
| 5,063,908 | November, 1991 | Collins | 128/17; 128/DIG.26 |
| 4,971,036 | November, 1990 | Collins | 128/17; 128/18 |
| 5,868,668 | February, 1999 | Weiss | 600/224; 600/221 |
| 5,392,764 | February | Swanson, et al. | 128/3; 128/9; 606/197 |
| 5,395,354 | Mar. 7, 1995 | Vancaillie | 604/317; 604/327; 604/329 |
| 5,873,820 | Feb. 23, 1999 | Norell | 600/220; 600/223 |
| 5,072,720 | Dec. 17, 1991 | Francis, et al. | 128/17; 606/198 |
| 5,499,964 | Mar. 19, 1996 | Beck, et al. | 600/220; 600/223; 600/205 |
| 4,766,887 | Aug. 30, 1988 | Cecil, Jr., et al. | 128/17; 128/345 |
| 5,785,648 | Jul. 28, 1998 | Min | 600/206; 600/223; |
| 5,231,973 | Aug. 3, 1993 | Dickie | 128/17 |
| 4,638,792 | Jan. 27, 1987 | Burgin | 128/6; 128/18 |
| 4,619,248 | Oct. 28, 1986 | Walsh | 128/18; 362/109 |
| 3,985,125 | Oct. 12, 1976 | Rose | 128/17 |
| 4,206,750 | Jun. 10, 1980 | Kaivola | 128/17; 128/341 |
| 4,385,626 | May 31, 1983 | Danz | 128/17 |
| 5,318,010 | Jun. 7, 1994 | Lundberg | 128/17; 128/20 |
| 5,545,122 | Aug. 13, 1996 | Spruill | 600/222; 600/186 |
| 4,597,382 | Jul. 1, 1986 | Perez, Jr | 128/17; 128/303.1 |
| 4,562,832 | January | Wilder, et al. | 128/20; 128/18 |
| 5,997,474 | Dec. 7, 1999 | Batchelor | 600/220; 600/222 |
| 4,899,734 | Feb. 13, 1990 | Gelley | 128/17; 81/318 |
| 5,865,729 | Feb. 2, 1999 | Meehan | 600/207; 600/208 |
| 5,716,329 | Feb. 10, 1998 | Dieter | 600/210; 600/201 |
| 5,377,667 | Jan. 3, 1995 | Patton | 128/3; 128/20 |
| 5,007,409 | Apr. 16, 1991 | Pope | 128/17; 128/3 |

Other References

General Catalogue, Aesculap AG & CO. KG. 78532 TUTLINGEN/GERMANY Collin Page 538 Cusco Page 540 Semm Page 541. Grave page 542. Pederson Page 542 Edition (publication) 9–998.

Catalogue Loop Surgery Premier Medical Products. Speculums: Graves. Pederson. Weisman—Grace. Premier Evacuator.

What is claimed is:

1. A disposable speculum, made of transparent plastic material, comprising;

an upper convex sheet having an internal surface with three grooves formed transversely in the internal surface connected together by grooves extending substantially parallel to the longitudinal axis of the sheet, with one of the longitudinal grooves ending in a plug;

a lateral extension extending from the upper sheet obliquely downwards;

a mobile back handle pivotally connected to the upper sheet;

a mobile safety bar having prongs therealong, extending from the back handle and through a hole in the lateral extension;

a convex lower sheet having three interconnected grooves formed on the internal surface of the lower sheet and forming a drainage channel and ending in a cap;

a fixed front handle extending at a 90-degree angle from the lower sheet;

a light bulb on the internal surface of the upper sheet between two grooves, said bulb including thermal protection; and an aluminum reflective cover mounted in front on the light bulb.

2. The disposable speculum according to claim 1, wherein the upper sheet has an external convex shape, rounded edges and a concave internal surface.

3. The disposable speculum according to claim 1, wherein the hole in the lateral extension has a spring therein which engages the prongs on the safety bar.

4. The disposable speculum according to claim if, wherein the back handle is forked shaped comprising two legs at the upper end pivotally attached to the proximal end of the upper sheet and a handle shaped lower end having prongs on the sides with tip pointing downwardly away from the upper sheet and a button extending from the center of the lower end.

5. The disposable speculum according to claim 1, wherein the lower sheet has an convex external surface and rounded edges.

6. The disposable speculum according to claim 1, further comprising a plug attached to the right side of the upper sheet through which power is supplied to the light bulb.

7. The disposable speculum according to claim 1, wherein the internal surface of the upper sheet has an aluminum reflective coating.

* * * * *